US00RE45718E

(19) United States
(12) Reissued Patent
Kilgore et al.

(10) Patent Number: US RE45,718 E
(45) Date of Reissued Patent: Oct. 6, 2015

(54) SYSTEMS AND METHODS FOR REVERSIBLY BLOCKING NERVE ACTIVITY

(75) Inventors: Kevin L. Kilgore, Avon Lake, OH (US); Warren M. Grill, Chapel Hill, NC (US); Cameron C. McIntyre, Cleveland, OH (US); John T. Mortimer, Chagrin Falls, OH (US)

(73) Assignee: BOSTON SCIENTIFIC CORPORATION, Natick, MA (US)

(21) Appl. No.: 12/816,802

(22) Filed: Jun. 16, 2010

Related U.S. Patent Documents

Reissue of:
(64) Patent No.: 7,389,145
Issued: Jun. 17, 2008
Appl. No.: 10/468,642
PCT Filed: Feb. 20, 2002
PCT No.: PCT/US02/04887
§ 371 (c)(1),
(2), (4) Date: Feb. 17, 2004
PCT Pub. No.: WO02/065896
PCT Pub. Date: Aug. 29, 2002

U.S. Applications:
(60) Provisional application No. 60/269,832, filed on Feb. 20, 2001.

(51) Int. Cl.
*A61N 1/34* (2006.01)
*A61N 1/36* (2006.01)

(52) U.S. Cl.
CPC ..... *A61N 1/36071* (2013.01); *A61N 1/3605* (2013.01); *A61N 1/36164* (2013.01); *A61N 1/36171* (2013.01); *A61N 1/36178* (2013.01)

(58) Field of Classification Search
None
See application file for complete search history.

(56) References Cited

U.S. PATENT DOCUMENTS

| | | | | |
|---|---|---|---|---|
| 3,645,267 | A * | 2/1972 | Hagfors | 607/44 |
| 5,036,850 | A * | 8/1991 | Owens | 607/66 |
| 5,052,391 | A * | 10/1991 | Silberstone et al. | 607/46 |
| 5,167,229 | A | 12/1992 | Peckham et al. | 607/48 |
| 6,136,019 | A * | 10/2000 | Mower | 607/9 |
| 6,421,566 | B1 * | 7/2002 | Holsheimer | 607/46 |
| 6,735,475 | B1 * | 5/2004 | Whitehurst et al. | 607/46 |
| 6,871,099 | B1 * | 3/2005 | Whitehurst et al. | 607/46 |
| 2002/0055779 | A1 * | 5/2002 | Andrews | 623/11.11 |

OTHER PUBLICATIONS

Bowman et al., "Response of Single Alpha Motoneurons to High-Frequency Pulse Trains," Appl. Neurophysiol. 49: 121-138 (1986).
Shaker et al., "Reduction of Bladder Outlet Resistance By Selective Sacral Root Stimulation Using High-Frequency Blockade in Dogs: An Acute Study," Journal of Urology, vol. 160, 901-907, Sep. 1998.

* cited by examiner

*Primary Examiner* — Kennedy Schaetzle
(74) *Attorney, Agent, or Firm* — Tarolli, Sundheim, Covell & Tummino LLP

(57) ABSTRACT

Systems and methods for blocking nerve impulses use an implanted electrode located on or around a nerve. A specific waveform is used that causes the nerve membrane to become incapable of transmitting an action potential. The membrane is only affected underneath the electrode, and the effect is immediately and completely reversible. The waveform has a low amplitude and can be charge balanced, with a high likelihood of being safe to the nerve for chronic conditions. It is possible to selectively block larger (motor) nerve fibers within a mixed nerve, while allowing sensory information to travel through unaffected nerve fibers.

9 Claims, 5 Drawing Sheets

SYSTEMS AND METHODS FOR REVERSIBLY BLOCKING NERVE ACTIVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

*This application is a broadening reissue of Ser. No. 12/272,394, now U.S. Pat. No. 7,389,145, entitled "SYSTEMS AND METHODS FOR REVERSIBLY BLOCKING NERVE ACTIVITY," issued on Jun. 17, 2008, by KILGORE et al.*

This application is a national stage filing under 35 U.S.C. 371 of International Application PCT/US02/04887, filed Feb. 20, 2002, which claims priority from U.S. application Ser. No. 60/269,832, filed Feb. 20, 2001, the specifications of each of which are incorporated by reference herein. International Application PCT/US02/04887 was published under PCT Article 21(2) in English.

*GOVERNMENT FUNDING*

*This invention was made with government support under grant No. EB002091, awarded by the NIH-National Institute of Biomedical Imaging and Bioengineering. The government has certain rights in the invention.*

FIELD OF THE INVENTION

This invention relates to systems and methods for selectively blocking nerve activity in animals, including humans, e.g., to reduce the incidence or intensity of muscle spasms, treat spacticity, or for pain reduction.

BACKGROUND OF THE INVENTION

Spinal cord injury can lead to uncontrolled muscle spasms. Spasticity can also occur as a result of stroke, cerebral palsy and multiple sclerosis. Peripheral nerve injury can cause pain, such as neuroma pain.

Various nerve blocking techniques have been proposed or tried to treat spasms, spacticity, and pain. They have met with varying degree of success. Problems have been encountered, such as damage and destruction to the nerve, and the inability to achieve a differentiation of nerve blocking effects among large and small nerve fibers in a whole nerve.

SUMMARY OF THE INVENTION

The invention provides systems and methods for blocking nerve impulses using an implanted electrode located near, on, or in a nerve region. A specific waveform is used that causes the nerve membrane to become incapable of transmitting an action potential. The effect is immediately and completely reversible. The waveform has a low amplitude and can be charge balanced, with a high likelihood of being safe to the nerve for chronic conditions. It is possible to selectively block larger (motor) nerve fibers within a mixed nerve, while allowing sensory information to travel through unaffected nerve fibers.

The applications for a complete non-destructive nerve block are many. A partial or complete block of motor fiber activity can be used for the reduction of spasms in spinal cord injury, and for the reduction of spasticity in stroke, cerebral palsy and multiple sclerosis. A complete block of sensory input, including pain information, can be used as a method for pain reduction in peripheral nerve injury, such as neuroma pain. A partial or complete block of motor fiber activity could also be used in the treatment of Tourette's Syndrome.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that [fail] *fall* within the meaning and range of equivalency of the claims are therefore intended to be embraced by the claims.

DESCRIPTION OF THE PREFERRED EMBODIMENTS

The various aspects of the invention will be described in connection with providing nerve stimulation to cause the blocking of the transmission of action potentials along a nerve. That is because the features and advantages that arise due to the invention are well suited to this purpose. Still, it should be appreciated that the various aspects of the invention can be applied to achieve other objectives as well.

I. System Overview

Figure 1:
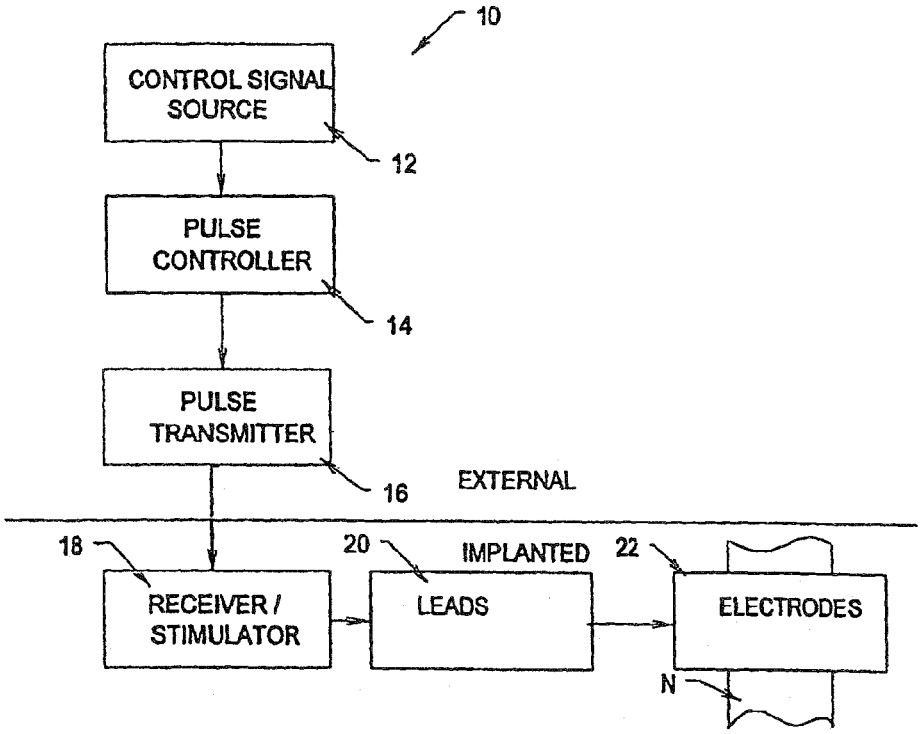
FIG. 1 is block diagram of a system that serves to generate a waveform that stimulates a targeted nerve region to cause either a partial or complete block of motor nerve fiber activity.

FIG. 1 shows a system 10 that makes possible the stimulation of a targeted nerve region N to cause either a partial or complete block of motor nerve fiber activity, which is non-destructive and immediately reversible. In use, the system 10 generates and distributes specific electrical stimulus waveforms to one or more targeted nerve regions N. The stimulation causes a blocking of the transmission of action potentials in the targeted nerve region N. The stimulation can be achieved by application of the waveforms near, on, or in *a* nerve region, using, e.g., [using] a nerve cuff electrode, [or] a nerve hook electrode, [or] an intramuscular electrode, or a surface electrode on a muscle or on the skin near a nerve region.

The system 10 comprises basic functional components including (i) a control signal source 12; (ii) a pulse controller 14; (iii) a pulse transmitter 16; (iv) a receiver/stimulator 18; (v) one or more electrical leads 20; and (vi) one or more electrodes 22.

As assembled and arranged in FIG. 1, the control signal source 12 functions to generate an output, typically in response to some volitional action by a patient, e.g., by a remote control switching device, reed switch, or push buttons on the controller 14 itself. Alternatively, the control signal source 12 can comprise myoelectric surface electrodes applied to a skin surface, that, e.g., would detect an impeding spasm based upon preestablished criteria, and automatically generate an output without a volitional act by a patient.

Figure 4:
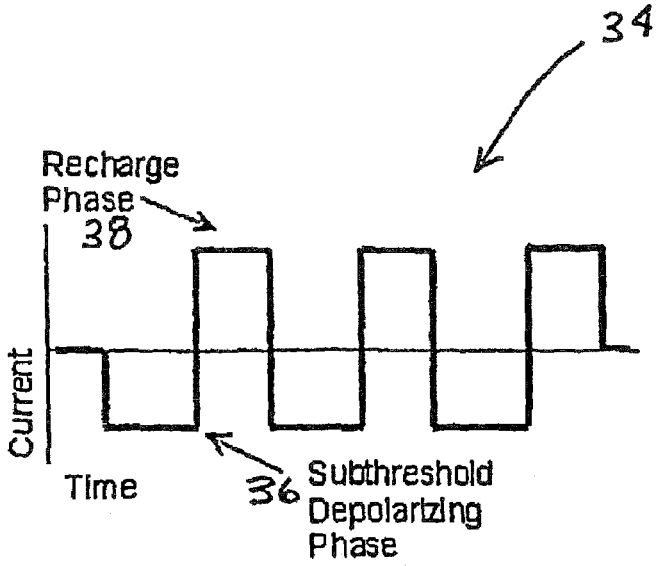
FIG. 4 is a graph showing the shape of the stimulation waveform that embodies features of the invention, which is constant current and delivered through [at] *an* electrode near the nerve and comprises a depolarizing cathodic pulse for blocking nerve conduction immediately followed by an anodic pulse.

In response to the output, the pulse controller 14 functions according to preprogrammed rules or algorithms, to generate a prescribed electrical stimulus waveform, which is shown in FIG. 4.

The pulse transmitter 18 functions to transmit the prescribed electrical stimulus waveform, as well as an electrical operating potential, to the receiver/stimulator 18. The receiver/stimulator 18 functions to distribute the waveform, through the leads 20 to the one or more electrodes 22. The one or more electrodes 22 store electrical energy from the electrical operating potential and function to apply the electrical signal waveform to the targeted nerve region, causing the desired inhibition of activity in the nerve fibers.

The basic functional components can be constructed and arranged in various ways. In a representative implementation, some of the components, e.g., the control signal source 12, the pulse controller 14, and the pulse transmitter 16 comprise external units manipulated outside the body. In this implementation, the other components, e.g., the receiver/stimulator 18, the leads 20, and the electrodes 22 comprise, implanted units placed under the skin within the body. In this arrangement, the pulse transmitter 16 can take the form of a transmitting coil, which is secured to a skin surface over the receiver/stimulator 18, e.g., by tape. The pulse transmitter 16 transmits the waveform and power through the skin to the receiver/stimulator 18 in the form of radio frequency carrier waves. Because the implanted receiver/stimulator 18 receives power from the external pulse controller 14 through the external pulse transmitter 16, the implanted receiver/stimulator 18 requires no dedicated battery power source, and therefore has no finite lifetime.

A representative example of this implementation (used to accomplish functional electrical stimulation to perform a prosthetic finger-grasp function) can be found is in Peckham et al U.S. Pat. No. 5,167,229, which is incorporated herein by reference. A representative commercial implementation can also be found in the FREEHAND™ System, sold by NeuroControl Corporation. (Cleveland, Ohio).

Figure 2:
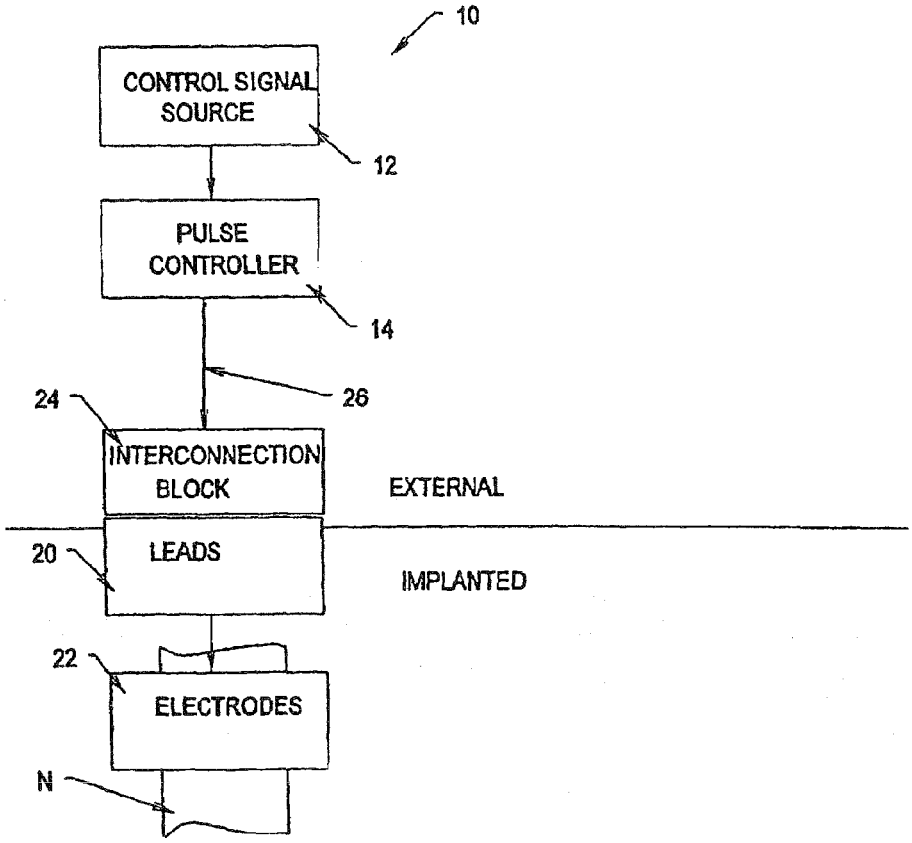
FIG. 2 is block diagram of an alternative embodiment of a system that serves to generate a waveform that stimulates a targeted nerve region to cause either a partial or complete block of motor nerve fiber activity.

In an alternative arrangement (see FIG. 2), the leads 20 can be percutaneously installed and be coupled to an external interconnection block 24 taped to the skin. In this arrangement, the pulse transmitter 16 is directly coupled by a cable assembly 26 (see FIG. 3, also) to the interconnection block 24. In this arrangement, there is no need for a pulse transmitter 16 and receiver/stimulator 18. A representative commercial example of this implementation (used to achieve neuromuscular stimulation to therapeutically treat shoulder subluxation and pain due to stroke) can be found in the StIM™ System, sold by NeuroControl Corporation (Cleveland, Ohio).

II. The Pulse Controller

Figure 3:
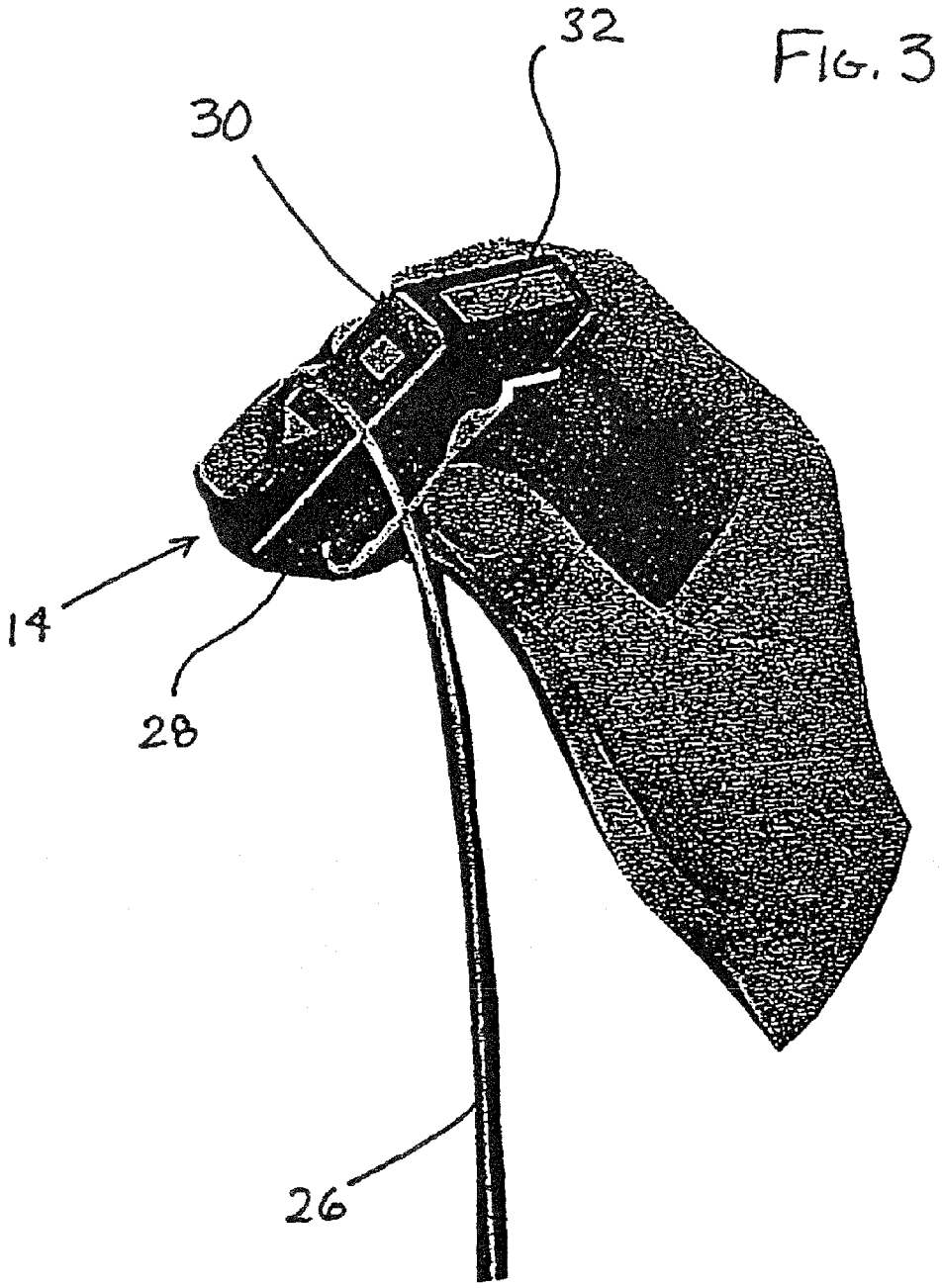
FIG. 3 is an enlarged view of a pulse controller that can be used in association with the system shown in FIG. 1 or FIG. 2, the pulse controller including a microprocessor that generates the desired stimulation waveform.

The pulse controller 14 is desirably housed in a compact, lightweight, hand held housing 28 (see FIG. 3). The controller 14 desirably houses a microprocessor 30. Desirably, the microprocessor 30 carries imbedded code, which expresses the pre-programmed rules or algorithms under which the desired electrical stimulation waveform is generated in response to input from the external control source 12. The imbedded code can also include pre-programmed rules or algorithms that govern operation of a display and keypad on the controller 14 to create a user interface 32.

A. The Desired Electrical Stimulation Waveform

The waveform 34 that embodies features of the invention is shown in FIG. 4. A stimulus provided by this waveform 34 is delivered to a nerve N through the electrodes 22 located on or around the nerve N. The waveform 34, when applied, places the nerve fiber membrane into a state in which it is unable to conduct action potentials.

The specific electrical stimulus waveform 34 that can be applied to cause a blocking of the transmission of action potentials along the nerve has two phases 36 and 38 (see FIG. 4).

The first phase 36 produces subthreshold depolarization of the nerve membrane through a low amplitude cathodic pulse. The first phase 36 can be a shaped cathodic pulse with a duration of 0.1 to 1000 millisecond and a variable amplitude between 0 and 1 milliamp. The shape of the pulse 36 can vary. It can, e.g., be a typical square pulse, or possess a ramped shape. The pulse, or the rising or falling edges of the pulse, can present various linear, exponential, hyperbolic, or quasi-trapezoidal shapes.

The second phase 38 immediately follows the first pulse 36 with an anodic current. The second anodic phase 38 has a higher amplitude and shorter duration than the first pulse 36. The second pulse 38 can balance the charge of the first phase 36; that is, the total charge in the second phase 38 can be equal but opposite to the first phase 36, with the second phase having a higher amplitude and shorter duration. However, the second pulse 38 need not balance the charge of the first pulse 36. The ratio of the absolute value of the amplitudes of the second phase 38 compared to the first phase 36 can be, e.g., 1.0 to 5.0. Because of the short duration of the anodic phase 38, the nerve membrane does not completely recover to the non-polarized state.

This biphasic pulse is repeated continuously to produce the blocking stimulus waveform. The pulse rate will vary depending on the duration of each phase, but will be in range of 0.5 Hz up to, 10 KHz. When this stimulus waveform 34 is delivered at the appropriate rate, typically about 5 kHz, the nerve membrane is rendered incapable of transmitting an action potential. This type of conduction block is immediately reversible by ceasing the application of the waveform.

Larger nerve fibers have a lower threshold for membrane depolarization, and are therefore blocked at low stimulus amplitudes. As a result, it is possible to block only the largest nerve fibers in a whole nerve, while allowing conduction in the smaller fibers. At higher stimulus amplitudes, all sizes of fibers can be blocked completely.

Figure 5:
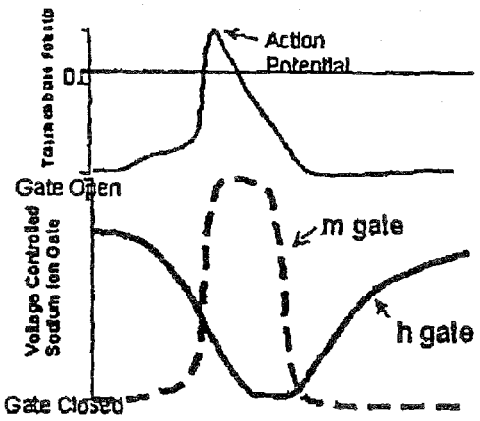
FIG. 5 is a diagram depicting the presumed action of the voltage controlled sodium ion gates during propagation of an action potential along a nerve. The top trace shows the transmembrane potential and the bottom trace shows the activity of the sodium gates during the same time period. The action potential begins when the m gates, which have a fast response time, open completely. The h gates, which respond more slowly, begin to close, which begins to restore the transmembrane potential. As the potential decreases, the m gates close and the h gates return to their resting position (partially open)

The physiological basis on which the waveform 34 is believed to work can be described [.] using the values of the sodium gating parameters, as shown in FIG. 5. The unique ability of the nerve axon to transmit signals is due to the presence of voltage controlled ion channels. The function of the sodium ion channels are influenced by two gates. One gate responds quickly to voltage changes, and is frequently termed the "m" gate. The other gate responds more slowly to voltage changes, and is termed the "h" gate. When the nerve is in, the rest condition, the m gates are almost completely closed, while the h gates are partially opened. When an action potential propagates along the axon, the m gates open rapidly, resulting in a rapid depolarization of the nerve membrane. The h gates respond by slowly closing. The membrane begins to repolarize, and the m gates begin to close rapidly. At the end of action potential generation, the m gates have returned to their initial state and the nerve membrane is slightly more polarized than at rest. The h gates return more slowly to their resting values, producing a period of reduced excitability which is referred to as the refractory period. The same series of events can be initiated by an externally applied cathodic (depolarizing) stimulus pulse. This is the basis for electrical stimulation of nerves.

Figure 6:
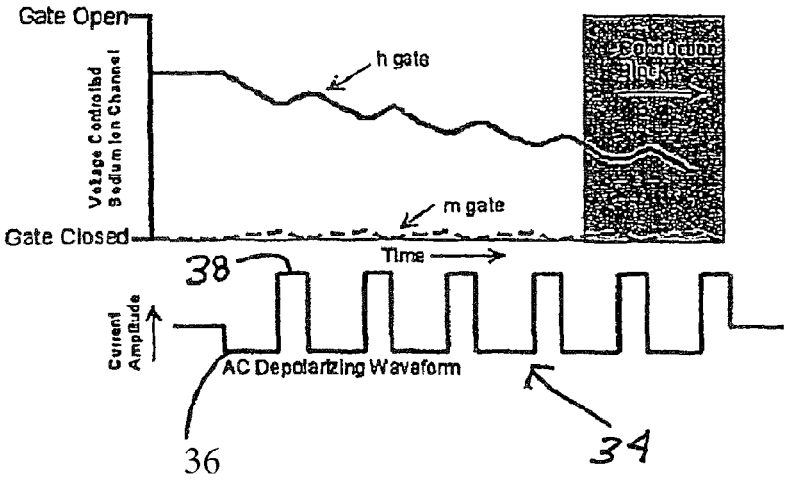
FIG. 6 is a diagram showing the action of the depolarizing waveform shown in FIG. 4, which is also shown in FIG. 6 below the upper graph, on the nerve membrane dynamics. The first cathodic, pulse causes the h gate to close and the m gate to open slightly. The anodic phase, which is shorter in duration, causes the m gate to return to the fully open state, but the h gate, because it responds more slowly, does not return completely to its resting value. As subsequent pulses are delivered, the h gate progressively closes, which causes the membrane to become inactivated. When the h gate is sufficiently closed, the nerve membrane can no longer conduct an action potential.

The waveform 34 of the invention makes use of the different relative responses of the two types of sodium ion channel gates. The first phase 36 of the waveform 34 is a subthreshold depolarizing pulse. The nerve membrane response is shown in FIG. 6. The h gates begin to slowly close during the first phase, while the m gates respond by opening only slightly. As long as the initial phase is maintained below the activation threshold for the nerve, the m gates will exhibit only a small response. If the depolarizing pulse 36 is maintained for long periods of time, the h gates will eventually close to the point that the membrane is no longer able to transmit an action potential.

The second phase 38 of the waveform 34 is a hyperpolarizing pulse of shorter duration than the initial depolarizing pulse. The effect of this pulse 38 is to cause the m gates to close completely and the h gates begin to slowly open. However, since this phase 38 is shorter than the first phase 36, the h gates do not return to their resting levels by the end of the phase 38. A second pulse of the waveform 34 of the same shape is then delivered to the nerve. The depolarization of the first phase 36 results in further closing of the h gates, with slight opening of the m gates. Some opening of the h gates again occurs with the second hyperpolarizing phase 38 of the pulse, but recovery back to the initial value does not occur. With subsequent pulses, the h gate progressively nears complete closing, while the m gate varies slightly between fully closed and slightly open. Due to the dynamics of the h gate, it will not fully close, but will continue to oscillate with each pulse near the fully closed condition. With both the m gate and the h gate nearly closed, the nerve membrane is now incapable of conducting action potentials. The nerve is effectively blocked.

This block can be maintained indefinitely by continuously delivering these pulses to the nerve. The block is quickly reversible when the stimulation is stopped. The h and m gates will return to their resting values within a few milliseconds, and the nerve will again be able to transmit action potentials.

Larger nerve fibers will have a lower threshold for subthreshold depolarizing block. Therefore, when the blocking waveform is delivered to a whole nerve, only the largest nerve fibers will be blocked. This provides a means of selective block, allowing a block of motor activation without affecting sensory information, which travels along the smaller nerves.

Figure 7:
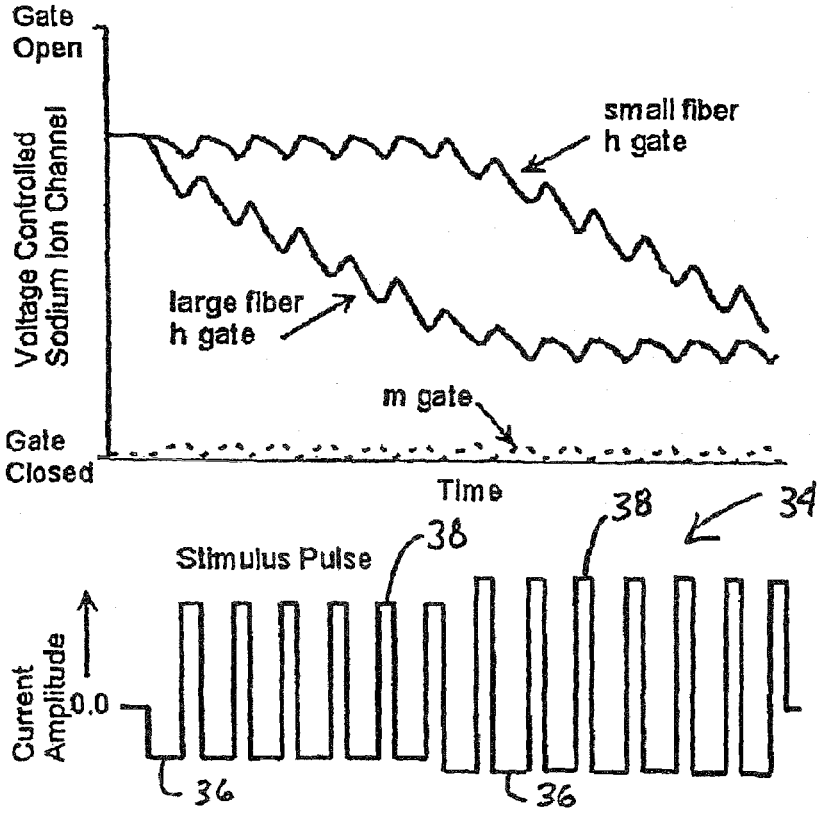
FIG. 7 is a diagram depicting the progressive block of two different nerve fiber diameters, the larger fiber responding to the lower amplitude depolarizing pulse (shown in the lower half of the diagram). The h gate is closed by this waveform and the large nerve fiber becomes inactive. The stimulus amplitude can then be increased so that inactivation of the smaller fiber can take place.

In order to generate a block of smaller nerve fibers in a large nerve, the amplitude of the waveform can be increased. As the amplitude is increased, the first phase of the waveform may produce a stimulated action potential in the larger nerves. However, because of the nerve membrane dynamics, it is possible to gradually increase the stimulus amplitude over time with each successive pulse, until even the smallest nerve fibers are blocked. This, is shown in FIG. 7. Very low amplitude pulses are used to put the membrane of the largest nerve fibers into an unexcitable state over the course of a few pulses. Once these largest fibers are at a steady state, they will not be activated even by very large cathodic pulses. At this point, the blocking stimulus amplitude can be increased so that it produces the closed h and m gate response in the smaller nerve fibers. The amplitude can be progressively increased until all nerve fibers are blocked. This progressive increase can occur rather quickly, probably within a few hundred milliseconds. This mechanism also serves to underscore the possibility of selective blocking of fibers of largest size using this waveform.

EXAMPLE 1

Neuroma Pain

A system 10 such as shown in FIG. 1 can be used to block neuroma pain association with an amputated arm of leg. In this arrangement, one or more electrodes 22 are secured on, in, or near the neuroma. The pulse controller 14 can comprise a handheld, battery powered stimulator having an on-board microprocessor. The microprocessor is programed by a clinician to generate a continuous waveform that embodies features of the invention, having the desired amplitude, duration, and shape to block nerve impulses, in the region of the neuroma. The pulse controller 14 can be coupled to the electrode, e.g., by percutaneous leads, with one channel dedicated to, each electrode used. A control signal source 12 could comprise an on-off button on the stimulator, to allow the individual to suspend or continue the continuous application of the waveform, to block the neuroma pain. No other special control functions would be required.

EXAMPLE 2

Muscle Spasms Due to Spinal Cord Injury, Cerebral Palsy, or Tourett's Syndrome A system 10 like that shown in FIG. 1 can be used to block muscle spasms due to, e.g., a spinal cord injury, cerebral palsy, or tourett's syndrome. In this arrangement, one or more electrodes 22 are secured on, in, or near the nerve or nerves affecting the muscle spasms. As in Example 1, the pulse controller 14 can comprise a handheld, battery powered stimulator having an on-board microprocessor. The microprocessor is programed by a clinician to generate a continuous waveform that embodies features of the invention, having the desired amplitude, duration, and shape to block nerve impulses in the region of the muscle spasms. As in Example 1, the pulse controller 14 can be coupled to the electrode, e.g., by percutaneous leads, with one channel dedicated to each electrode used. A control signal source 12 could comprise an on-off button on the stimulator, to allow the individual to suspend or continue the continuous application of the waveform, to block the muscle spasms. Thus, for example, the individual could turn the stimulator off during sleep, or during a period where muscle function is otherwise desired. The selective stimulation-off feature also allows the individual to perform muscle functions necessary to maintain muscle tone. In this arrangement, no other special control functions would be required.

Alternatively, the control signal source 12 could comprise an electrode to sense electroneurogram (ENG) activity in the region where muscle spasms occur. The electrode could comprise the stimulation electrode itself, or a separate ENG sensing electrode. The electrode detects ENG activity of a predetermined level above normal activity (e.g., normal ENG activity X10), identifying a spasm episode. In this arrangement, the microprocessor is programed to commence generation of the desired waveform when the above normal ENG activity is sensed. The microprocessor is programmed to continue to generate the waveform for a prescribed period of time (e.g., 1 minute) to block the spasm, and then cease waveform generation until another spasm episode is detected. In this arrangement, the stimulator can also include a manual on-off button, to suspend operation of the stumulator in response to input from the sensing electrode.

EXAMPLE 3

Block Uncoordinated Finger Flexure Spasms Due to Multiple Sclerosis or Stroke A system 10 like that shown in FIG. 1 can be used to block finger flexure spasms due to, e.g., a multiple sclerosis or stroke. In this arrangement, one or more epimysial and intramuscular electrodes 22 are appropriately implanted by a surgeon in the patient's arm. The implanted electrodes 22 are positioned by the surgeon by conventional surgical techniques to block conduction of impulses to finger flexure muscles. As in Example 1, the pulse controller 14 can comprise a handheld, battery powered stimulator having an on-board microprocessor. The microprocessor is programed by a clinician to generate a continuous waveform that embodies features of the invention, having the desired amplitude, duration, and shape to provide a low level block of nerve impulses to the finger flexure muscles. A control signal source 12 could comprise an on-off button on the stimulator, to allow the individual to select the continuous application of the waveform, e.g., while the individual is opening or closing their hand.

Alternatively, the control signal source 12 could comprise an electrode to sense electromyogram (EMG) activity in the finger flexor muscles. The electrode detects EMG activity during stimulated activation of the finger extensor muscles. If this activity exceeds a preset level (e.g. 30% maximum contraction level), the microprocessor is programmed to commence generation of the desired waveform to block some or all of the finger flexor muscle activity. The microprocessor can be programmed to deliver a block proportional to the level of EMG activity, or to deliver a block for a prescribed period of time, or to deliver a block as determined through a combination of parameters (e.g., EMG activity from multiple muscles in the arm).

In another alternative embodiment, the control signal source 12 can comprise comprises a mechanical joy stick-type control device, which senses movement of a body region, e.g., the shoulder. Movement of the body region in one prescribed way causes the microprocessor to commence generation of the desired waveform. Movement of the body region in another prescribed way causes the microprocessor to cease generation of the desired waveform.

In either alternative arrangements, the stimulator can also include a manual on-off button, to suspend operation of the stumulator in response to the external inputs.

Various features of the invention are set forth in the following claims.

The invention claimed is:

[1. A method for selectively blocking activity of a nerve in an animal by application of an electric current, said method comprising: generating an electrical waveform having a first phase with a first polarity, a first duration, and a first amplitude, that produces subthreshold depolarization of the nerve membrane and a second phase after the first phase that has a second polarity, a second duration, and a second amplitude; and applying the waveform to a targeted nerve region, wherein the phases of said waveform are delivered at a rate of at least 5 kilohertz (kHz), and the ratio of the amplitude of the second phase to the amplitude of the first phase is about 1:1 to about 1:5.]

[2. The method as set forth in claim 1, wherein said first and second phases are charge balanced.]

[3. The method as set forth in claim 1, wherein said pulses of said waveform are delivered at a rate of between about 5 kilohertz (kHz) and 10 kilohertz (kHz) inclusive.]

[4. The method as set forth in claim 1, wherein said second amplitude is greater than said first amplitude.]

[5. The method as set forth in claim 1, wherein said second duration is less than said first duration.]

[6. The method as set forth in claim 1, wherein at least one of said first and second amplitude are increased over time to block conduction of said action potential in progressively smaller nerve fibers.]

[7. The method as set forth in claim 1, wherein the first amplitude is about 0 to 1 milliamps.]

[8. A method for selectively blocking conduction of an action potential in a nerve of an animal such as a human, said method comprising: delivering an electrical waveform to a nerve, said waveform comprising a series of bi-phasic pulses that, when applied to said nerve, block conduction of an action potential by said nerve, wherein said nerve comprises h gates and m gates and wherein said bi-phasic pulses of said waveform close said h gates and said m gates sufficiently to block said nerve from conducting said action potential, wherein each pulse of said electrical waveform comprises: a first phase having a first polarity, a first duration and a first amplitude, said first amplitude less than an activation threshold of said nerve; and, a second phase having a second polarity, a second duration and a second amplitude, wherein the pulses of said waveform are delivered at a rate of at least 5 kilohertz (kHz), and the ratio of the amplitude of the second phase to the amplitude of the first phase is about 1:1 to about 1:5.]

[9. The method as set forth in claim 8, wherein said second amplitude is greater than said first amplitude.]

[10. The method as set forth in claim 8, wherein said second duration is less than said first duration.]

[11. The method as set forth in claim 8, wherein said pulses of said waveform are delivered at a rate of between about 5 kilohertz (kHz) and 10 kilohertz (kHz) inclusive.]

[12. The method as set forth in claim 8, wherein at least one of said first and second amplitude are increased over time to block conduction of said action potential in progressively smaller nerve fibers.]

[13. The method as set forth in claim 8, further comprising: monitoring at least one of electroneurogram (ENG) activity and electromyogram (EMG) activity of the animal of which said nerve is a part; and, using said at least one of said electroneurogram and electromyogram activity to derive said waveform.]

[14. The method as set forth in claim 8, wherein said first phase is cathodic and the second phase is anodic.]

*15. A method, comprising:*

*generating a steady state electrical waveform,*

*where the steady state electrical waveform has a first phase having a first polarity, a first duration, and a first amplitude, the first phase being a cathodic, depolarizing phase configured to depolarize a nerve,*

*where the steady state electrical waveform has a second phase having a second polarity, a second duration, and a second amplitude, the second phase being an anodic, repolarizing phase configured to repolarize the nerve,*

*where the ratio of the first amplitude to the second amplitude is 1:1 to 1:5,*

*where each of the first phase and the second phase has a frequency in the range of 5 kiloHertz (KHz) up to 10 KHz, and*

*applying an electric current to the nerve in an animal according to the steady state waveform, where applying the electric current comprises:*

*selectively, repetitively, alternately applying the first phase of the steady state electrical waveform to the nerve and then applying the second phase of the steady state electrical waveform to the nerve for a period of time sufficient to arrest signal transmission through the nerve, and*

*arresting signal transmission in progressively smaller nerve fibers in the nerve by altering, over time, at least one of the first amplitude and the second amplitude.*

*16. The method of claim 15, where the first amplitude is about 0 milliamps to 1 milliamps.*

*17. A method, comprising:*

*selectively blocking conduction of an action potential in a nerve in an animal by selectively, repetitively delivering a series of bi-phasic pulses to the nerve,*

*where a member of the series of the bi-phasic pulses has a first phase and a second phase, the first phase having a first polarity, a first duration, and a first amplitude, the first phase being a cathodic, depolarizing phase,*

*the second phase having a second polarity, a second duration, and a second amplitude, the second phase being an anodic, repolarizing phase,*

*each of the first phase and the second phase being delivered at a frequency in the range of at least 5 KHz up to 10 KHz,*

*where the ratio of the first amplitude to the second amplitude is 1:1 to 1:5, and*

*selectively blocking conduction of action potentials in progressively smaller nerve fibers in the nerve by altering, over a period of time, one or more of the first amplitude and the second amplitude.*

*18. The method of claim 17, where the first duration is greater than the second duration.*

*19. The method of claim 17, comprising:*

*acquiring, from the animal, one or more of, electroneurogram (ENG) data, and electromyogram (EMG) data; and*

*configuring the electrical waveform as a function of one or more of, the ENG data, and the EMG data.*

*20. The method of claim 17, where selectively blocking conduction of the action potential down regulates neural activity in the animal.*

*21. The method of claim 20, comprising down regulating neural activity in an amount sufficient to treat a disease or condition.*

*22. The method of claim 21, the disease or condition being one of, neuroma, spasticity, and muscle spasms.*

*23. A method, comprising:*

*selectively blocking conduction of an action potential in a nerve in an animal by selectively, repetitively delivering a series of bi-phasic pulses to the nerve,*

*where a member of the series of the bi-phasic pulses has a first phase and a second phase, the first phase having a first polarity, a first duration, and a first amplitude, the first phase being a cathodic, depolarizing phase,*

*the second phase having a second polarity, a second duration, and a second amplitude, the second phase being an anodic, repolarizing phase,*

*each of the first phase and the second phase being delivered at a frequency in the range of at least 5 KHz up to 10 KHz,*

*where the ratio of the first amplitude to the second amplitude is 1:1 to 1:5, and*

*where the first duration is greater than the second duration.*

* * * * *